US00RE37287E

(19) United States
(12) Reissued Patent
Lebrun et al.

(10) Patent Number: US RE37,287 E
(45) Date of Reissued Patent: Jul. 17, 2001

(54) CHIMERIC GENE FOR THE TRANSFORMATION OF PLANTS

(75) Inventors: Michel Lebrun, Montpellier (FR); Bernard Leroux, Raleigh, NC (US); Alain Sailland, Lyons (FR)

(73) Assignee: Aventis Cropscience S.A., Lyons (FR)

(21) Appl. No.: 09/025,042

(22) Filed: Feb. 17, 1998

Related U.S. Patent Documents

Reissue of:
(64) Patent No.: 5,633,448
Issued: May 27, 1997
Appl. No.: 08/477,581
Filed: Jun. 7, 1995

U.S. Applications:

(62) Division of application No. 08/251,621, filed on May 31, 1994, now Pat. No. 5,510,471, which is a continuation of application No. 07/846,211, filed on Mar. 4, 1992, now abandoned.

(30) Foreign Application Priority Data

Mar. 5, 1991 (FR) ..... 91 02872

(51) Int. Cl.[7] ..... A01H 5/00; C12N 5/04; C12N 15/82

(52) U.S. Cl. ..... 800/278; 800/320.1; 800/300; 435/320.1; 435/252.3; 435/468; 435/418; 435/419; 536/24.1; 536/23.4; 536/23.2; 536/23.7

(58) Field of Search ..... 800/300, 278, 800/320.1; 435/320.1, 252.3, 69.1, 468, 418, 419; 536/24.1, 23.4, 23.2, 23.7

(56) References Cited

U.S. PATENT DOCUMENTS

| | | | |
|---|---|---|---|
| 4,535,060 | 8/1985 | Comai | 435/252.33 |
| 4,801,540 | 1/1989 | Hiatt et al. | 435/411 |
| 4,940,835 | 7/1990 | Shah et al. | 800/288 |
| 4,962,028 | 10/1990 | Bedbrook et al. | 800/278 |
| 5,073,677 | 12/1991 | Heimer et al. | 800/300 |
| 5,188,642 | 2/1993 | Shah et al. | 47/58.1 |
| 5,254,799 | 10/1993 | De Greve et al. | 800/302 |
| 5,258,300 | 11/1993 | Glassman et al. | 800/288 |
| 5,312,910 | 5/1994 | Kishore et al. | 536/23.2 |
| 5,349,123 | 9/1994 | Shewmaker | 800/284 |
| 5,463,175 | 10/1995 | Barry et al. | 800/300 |
| 5,489,520 | 2/1996 | Adams et al. | 800/293 |
| 5,498,830 | 3/1996 | Barry et al. | 800/281 |
| 5,530,188 | 6/1996 | Ausich et al. | 800/282 |
| 5,538,878 | 7/1996 | Thomas et al. | 800/288 |
| 5,554,798 | 9/1996 | Lundquist et al. | 800/300.1 |
| 5,559,024 | 9/1996 | Leroux et al. | 435/252.3 |
| 5,597,717 | 1/1997 | Guerineau et al. | 800/288 |
| 5,608,149 | 3/1997 | Barry et al. | 800/284 |
| 5,633,444 | 5/1997 | Guerineau et al. | 800/300 |

FOREIGN PATENT DOCUMENTS

| | | |
|---|---|---|
| 0 189 707 B1 | 8/1986 | (EP) . |
| 0 218 571 B1 | 4/1987 | (EP) . |
| 0 337 899 | 10/1989 | (EP) . |
| WO 88/02402 | 4/1988 | (WO) . |

OTHER PUBLICATIONS

B. Reiss et al (1989), "Effect of Mutations on the Binding and Translocation Functions of a Chloroplast Transit Peptide", *Proc. Natl Acad Sci USA*, 86: 886–890.

B. Mazur et al (1989), "The Development of Herbicide Resistant Crops", *Annu. Rev. Plant Physiol Plant Mol. Biol* 40: 441–470.

S. Smeekens et al (1990) "Protein Transport into and Within Chloroplasts", *TIBS* 15: 73–76.

LeBrun et al "Nucleotide Sequence of a Gene Encoding Corn Ribulose–1,5 Bisphosphate Carboxylase/Oxygenase Small Subunit (rbcs)", *Nucleic Acids Research*, vol. 15, No. 10 (1987), p. 4360.

Waksman "Nucleotide sequence of a gene encoding sunflower ribulose–1,5bisphosphate carboxylase/oxygenase small subunit (rbcs)", *Nucleic Acids Research*, vol. 15, No. 17 (1987), p. 7181.

L. Comai, et al (1988), "Chloroplast Transport of a Ribulose Bisphosphate Carboxylase Small Subunit–5– Enolpyruvyl 3–Phosphoshikimate Synthase Chimeric Protein Requires Part of the Mature Small Subunit in Addition to the Transit Peptide", *The Journal of Biological Chemistry* vol. 263, No. 29 Issue of October 15, pp. 15104–15109.

Wasmann, Reiss, Bartlett and Bohnert, (1986) "The Importance of the Transit Peptide and the Transported Protein for Protein Import into Chloroplasts", *Mol Gen Genet*, 205: 446–453.

J. Bennett, (1982), "Sic Transit Peptide", *Trends in Biotechnology, Elsevier Biomedical Press.*

J. Bryant, (1985), "Targetting Proteins Into Subcellular Organelles", *Trends in Biotechnology, Elsevier Biomedical Press*, p. 13.

E. Bell & L. McIntosh, (1984) "Molecular Basis of Transit Peptide Function", *Annual Mtg. of the Am.Soc.Plant Phys.*, Davis.

S. Smith et al., (1983), "Characterization of three cDNA clones encoding different mRNAs for the precursor to the small subunit of wheat ribulose bisphosphate carboxylase", *Nucleic Acids Research*, vol. 11 No. 24 pp. 8719–8734.

(List continued on next page.)

*Primary Examiner*—Elizabeth F. McElwain
(74) *Attorney, Agent, or Firm*—Connolly, Bove, Lodge & Hutz LLP

(57) ABSTRACT

Chimeric gene for conferring to plants an increased tolerance to a herbicide having as its target EPSPS comprises, in the direction of transcription, a promoter region, a transit peptide region, a coding sequence for glyphosate tolerance and a polyandenylation signal region, wherein the transit peptide region comprises, in the direction of translation, at least one transit peptide of a plant gene encoding a plastid-localized enzyme and then a second transit peptide of a plant gene encoding, a plastid-localized enzyme. Production of glyphosate-tolerant plants is disclosed.

24 Claims, No Drawings

OTHER PUBLICATIONS

A. Cashmore et al (1985) "Import of Polypeptides into Chloroplasts", *Bio/Technology*, vol. 3 Sep. 1985 pp. 803–807.

G. Van de Broeck et al, (1985), "Targeting of a Foreign Protein to Chloroplasts by Fusion to the Transit Peptide from the Small Subunit of Ribulose 1,5–bisphosphate Carboxylase", *Nature* (*Lond*), vol. 313 pp. 358–363.

R. Broglie et al., (1983), "Structural Analysis of Nuclear Genes Coding for the Precursor to the Small Subunit of Wheat Ribulose–1,5 Bisphosphate Carboxylase", *Bio/Technology*, Mar. 1983 pp. 55–61.

B. Reiss et al, (1985), "Transport of Foreign Proteins into Chloroplasts: Functional Domains of the Rbcs Transit Peptide", *3d Joint Meeting of Biochemical Societies, Basel*, vol. 36 p. 839.

G. Coruzzi et al, (1983) "Expression of Nuclear Genes Encoding the Small Subunit of Ribulose–1,5–Bisphosphate Carboxylase", *NATO Adv. Sci. Inst. Serv. A*, pp. 47–59.

B. Leroux et al, (1988), "A New Selectable Marker to Study Gene Expression in Plants", *Journal of Cellular Biochemistry*, Abstract L513 at p. 201.

B. Martineau et al, (1988), "Expression of a C3 Plant Rubisco SSU Gene in Regenerated C4 Plants", *Journal of Cellular Biochemistry*, Abstract L514 at p. 201.

P.H. Schreier et al, (1985), "The Use of Nuclear–Encoded Sequences to Direct the Light–Regulated Synthesis and Transport of a Foreign Protein into Plant Chloroplasts", *MBO Journal*, vol. 4, No. 1, pp. 25–32.

Reiss, B,; Wasmann C. C; Bohnert H.J.; Mol. Gen. Genet 209, (1), pp. 116–121; 1987, Abstract Only.

Kuntz M; Simons A., Schell J.; Schreier P.H., Mol. Gen. Genet 205 (3); 1986 454–460, Coden Meggeae Issn: 0026–8925, Abstract Only.

Schreier, P.H. Philos Trans R. Soc. London B Biol Sci 313 (1162), 1986, 429–432, "Use of Chimeric Genes Harboring . . . Chloroplasts", Abstract Only.

Kloesgen R. B., et al., Mol. Gen Genet 203 (2), 1986, 237–244, "Molecular Analysis of the Waxy Locus of Zea–Mays", Abstract Only.

Schreier P. H. et al.; Impact Gene Transfer Tech. Eukaryotic Cell Biol; (1984)) 91–102, "The Chloroplast genome, . . . Chloroplast Metabolism", Abstract Only.

Cioppa, G. della, et al., Bio/Technology, (1987) vol. 5, No. 6, pp. 579–584, 18 ref. "Targetting a herbicide–resistant enzyme . . . higher plants", Abstract Only.

Della–Cioppa G., et al, Proc. Natl. Acad. Sci USA 83 (18), 1986; 6873–6877; "Translocation of the Precursor . . . Higher Plants In–Vitro", Abstract Only.

Della–Cioppa G., et al; Fed. Proc. Fed. Am. Soc. Exp. Biol.; (1987) 46, 6 2109 "Targeting of a glyphosate–resistant . . . chloroplasts of higher plants", Abstract Only.

Della–Cioppa G. et al.; Bio/Technology; (1987) 5, 6, 579–84 Targeting a Herbicide–Resistent . . . Higher Plants, Abstract Only.

Scherer D. E., et al., Plant Mol Biol 9 (2) 1987; 127–134 "Isolation of a Complementary DNA . . . Spinach", Abstract Only.

Rose R. E. et al; Nucleic Acids Res.; (1987) 15, 17, 7197 "The Nucleotide Sequence of a cDNA . . . Compestris Seeds", Abstract Only.

Pichersky E.; et al. , Gene (AMST) 40 (2–3), 1985 247–258, "Molecular Characterization and Genetic . . . Esculentum Tomato", Abstract Only.

Broglie, R., et al., Bio/Technology, (1983) vol. 1, No. 1, pp. 55–61, 49 ref. "Structural Analysis of Nuclear Genes . . . Carboxylas", Abstract Only.

Coruzzi, Gloria, et al., J. Biol. Chem. (1983), 258(3), 1399–402, "Nucleotide Sequences of two pea cDNA . . . Polypeptide", Abstract Only.

Lamppa G. K., et al., Mol. Cell Biol 5 (6) 1985, 1370–1378, "Structure and Developmental Regulation . . . Polypeptide", Abstract Only.

Timko, Michael, P., et al., UCLA Symp. Mol. Cell. Biol., New. Ser. (1983), 12 (Plant Mol. Biol). 403–12, "Nuclear Genes Encloding . . . Complex From Pea", Abstract Only.

Smeekens, S., et al., Plant Mol Biol. 7 (6), 1986, 433–440, "Silene–Pratensis Complementary DNA . . . Carboxylase", Abstract Only.

Smeekens S., et al., Plant Molecular Biology, (1987), vol. 9, No. 4, pp. 377–388, "Import Into Chloroplasts . . . Plastocyanin Transit Peptides", Abstract Only.

Hageman J., et al., Feb. 2–8, 1987, J. Cell Biochem Suppl 0 (11 Part B), 64, "Important of Plastocyanin . . . Chloroplasts", Abstract Only.

Smeekens S., et al., Nature (Lond) 317 (6036) 1985, 456–468, "Sequence of the Precursor . . . Protein Plastocyanin", Abstract Only.

Smeekens, Sjef, et al., Nucleic Acids Res. (1985), 13(9), 3179–94, "The Plant Ferredoxin precursor . . . cDNA clone", Abstract Only.

Herrera–Estrella, L. et al., Second European Congress on Cell Biology, Jul. 6–11, 1986, ACTA Biol. Hung 37 (Suppl.), "The Roll of the Transit Peptide . . . Chloroplasts", Abstract Only.

Broeck, G. van den et al., Nature, UK, (1985) vol. 313, No. 6001, pp. 358–363, 56 ref. "Targeting of a foreign protein . . . carboxylase", Abstract Only.

Van Montagu, et al., Prod. Agents Ther. Genie Genet., Symp Satell. (1986), Meeting Date 1985, 59–63, "Plant Genetic Engineering", Abstract Only.

Herrera–Estralla, Mol. Biol. Photosynth. Appar. (1985), 397–405. "Use of chimeric genes to study light–inducible . . . Carboxylas", Abstract Only.

Wasmann C. C., et al., Annual Meeting of the American Society of Plant Physiologists, St. Louis, Missouri, Jul. 19–23, 1987, Plant Physiol 83 (4 Suppl). 1987, 55., "The Transit Peptide of the Precursor . . . Functional Regions", Abstract Only.

Lubben, T.H., Proc Natl. Acad. Sci, USA 83 (15) 1986, "Efficient In–Vitro Import of a Cytosolic . . . Chloroplasts", Abstract Only.

Keegstra K., et al., Symposium on Plant Membranes: Structure, Function, Biogenesis Held at the 16$^{th}$ Annual UCLS Meeting on Molecular and Cellular Biology, Feb. 8–13, 1987, J. Cell. Biochem Suppl 0 (11 Part B), 1987, 75, "Targeting of Proteins into Chloroplasts", Abstract Only.

Keegstra K., et al., Symposium on Plant Gene Systems & Their Biology Held at the 16$^{th}$ Annula UCLA Meeting on Molecular and Cellular Biology, Los Angelos, CA. Feb. 2–8, 1987, J. Cell Biochem Suppl 0 (11 Part B) 1987, "Tarteging of Proteins into and across Chloroplasts Membranes", Abstract Only.

Kohorn B. D., et al., Plant physiuol (Bethesda) 82 (4), 1986 1172–1174, "Chloroplast Import of Light–Harvesting . . . Transit Peptides", Abstract Only.

Karlin–Neuman, G.A., et al, EMBO (Eur. Mol. Biol Organ) J 5 (1) 1986, 9–14, "Transit Peptides of Neclear–Encoded . . . Acid Framework", Abstract Only.

Stiekema, Willem J., et al. Nucleic Acids Res. (1983), 11(22), 8051–61, "Nucleotide Sequence Encoding . . . from Lemna Bibba 1.g–3", Abstract Only.

Dunsmuir, Pamela, Nucleic Acids Res. (1985), 13(7), 2503–18; "The Petuna chlorophyll a/b/ . . . different gene families", Abstract Only.

Mayfield S.P., Proc. Natl Acad Sci USA 84 (3), 1987, 749–753, "Expression of the Nuclear Gene Encoding . . . Chlamydomonas–Reinhardtii", Abstract Only.

Rochaix, J.D., et al., Gene Manipulation Plant Imrpv., Stadler Genet., Symp., 16$^{th}$ (1984) 577–603, "Chlamydomonas reinhardii, a potential model . . . gene manipulation", Abstract Only.

Bell, Erin, Michigan State Univ., (1987) 121 pp. Avail.: Univ. Microfilms Int., Order No. DA8714299, from: Diss. Abstr. Int. B 1987, 48(3), 654, "A Molecular Analysis of ribulose . . . peptide function", Abstract Only.

Tyagi A.k et al., Mol. Gen. Genet 207 (2–3), 1987 288–293, "Nucleotide Sequence of complementary DNA . . . Complex From Spinach", Abstract Only.

Hodsperth R.L., et al., Proc Natl Acad Sci USA 83 (9), 1986, 2884–2888, "Genomic and Complementary DNA Clones . . . Members in leaves and roots", Abstract Only.

Hurt E. C., et al., EMBO (Eur Mol Biol Organ) J 5 (6), 1986, 1343–1350, "The Cleavable Pre–Sequence . . . Polypeptides into yeast mitochondria", Abstract Only.

Anderson, S., et al, Biochem J 240 (3), 1986, 709–716, "Synthesis of the Small Subunit . . . SP6 Promoter", Abstract Only.

Nierzwicki–Bauer S.A., et al., Proc. Natl. Acad Sci USA 81 (19), 1984, 5961–5965, "Contranscription of Genes Encoding . . . Cyanobactreium Anabaena", Abstract Only.

Pinck M., et al., Biochimie (Paris) 66 (7–8), 1984 539–546, "Complete Sequence of Oe of the Messenger RNA . . . Carboxylase EC–4.1.1.39 of Nicotiana–Sylvestris", Abstract Only.

Belford H.S., et al., J. Biol Chem 258 (7), 1983,4503–4510, "Phycobili Protein synthesis . . . Peptides of Phycocyanin", Abstract Only.

Martin P.G., et al., Aust J. Bot 31 (4), 1983, 395–410, "The Study of Plant Phylogeny Using Amino–Acid . . . Variability", Abstract Only.

Berry–Lowe S.L., et al., J. Mol. Appl. Genet 1 (6), 1982, 483–498, "the Nucleotide Sequence Expression . . . Glycine–Max", Abstract Only.

Ishiye M., et al., Febs (Fed Eurn Biochem Soc) Lett 124 (2), 1981, 233–236, "The High Iso Electric Point . . . Transit Peptide", Abstract Only.

Bennett J., Trends in Biochemical Sciences, (1982) vol. 7, No. 8, pp. 269, "Transit Peptide", Abstract Only.

Kaderbhai, N., et al., Biochem. Soc. Trans. (1987), 15(6), 1143–4, "Expression of the fusion protein . . . *Escherichia coli*", Abstract Only.

Gatenby, Anthony A., et al., Eur. J. Biochem. (1987), 168(1), 227–31, "Coexpression of both the maize . . . in *Escherichia coli*", Abstract Only.

Stayton, Mark, M., et al., Nucleic Acids Res. (1986), 14(24), 9781–96; "A novel chlorophyll a/b/ binding . . . precursor protein", Abstract Only.

CHIMERIC GENE FOR THE TRANSFORMATION OF PLANTS

Matter enclosed in heavy brackets [ ] appears in the original patent but forms no part of this reissue specification; matter printed in italics indicates the additions made by reissue.

This is a divisional of application Ser. No. 08/251,621, filed on May 31, 1994, now U.S. Pat. No. 5,510,471 which is a continuation of Ser. No. 07/846,211, filed on Mar. 4, 1992, now abandoned.

BACKGROUND OF THE INVENTION

The present invention relates to novel transit peptide DNA sequences, to novel chimeric genes and to their use in plants for conferring to them an increased tolerance to herbicides in general especially to those of the phosphonomethylglycine family. It also relates to the plant cells transformed by means of these genes, to the transformed plants regenerated from these cells as well as to the plants derived from crossbreedings using these transformed plants.

Glyphosate, sulfosate or fosametine are broad-spectrum systemic herbicides of the phosphonomethyl-glycine family. They act essentially as competitive inhibitors of 5-(enolpyruvyl)shikimate-3-phosphate synthase (EC 2.5.1.19) or EPSPS in relation to PEP (phosphoenolpyruvate). After their application to the plant, they are translocated inside the plant where they accumulate in the rapidly growing parts, in particular the caulinary and root apexes, causing the deterioration and even the destruction of sensitive plants.

Plastidial EPSPS, the main target of these products, is an enzyme of the aromatic amino acid biosynthesis pathway which is encoded by one or more nuclear genes and synthesised in the form of a cytoplasmic precursor and then imported into the plastids where it accumulates in its natural form.

The tolerance of plants to glyphosate and to products of the family is obtained by the stable introduction inside their genome of an EPSPS gene of plant or bacterial origin mutant or nonmutant with respect to the characteristics of the inhibition of the product of this gene by glyphosate. Given the mode of action of glyphosate and the degree of tolerance to glyphosate of the product of the genes used, it is useful to be able to express the product of translation of this gene so as to permit its substantial accumulation in plastids.

It is known, for example from American Patent U.S. Pat. No. 4,535,060, to confer to a plant a tolerance to a herbicide of the abovementioned type, in particular N-(phosphonomethyl)glycine or glyphosate, by introducing into the plant genome a gene encoding an EPSPS carrying at least one mutation making this enzyme more resistant to its competitive inhibitor (glyphosate), after localisation of the enzyme in the plastidial compartment. However, these techniques need to be improved in order to achieve greater reliability in the use of these plants under agronomic conditions.

SUMMARY OF THE INVENTION

In the present description, "plant" is understood as meaning any differentiated multicellular organism capable of photosynthesis and "plant cell" any cell derived from a plant and capable of forming undifferentiated tissues such as calluses or differentiated tissues such as embryos or plant sections, plants or seeds.

The subject of the present invention is the production of transformed plants having an increased tolerance to herbicides in general and especially to those of the phosphonomethylglycine family by regenerating cells transformed by means of novel chimeric genes comprising a gene for tolerance to these herbicides. The invention also relates to these novel chimeric genes, to the novel transit peptides which they contain as well as to the plants containing them which are made more tolerant by an accumulation of the mutant enzyme, in its mature form, in the plants.

More particularly, the subject of the invention is a chimeric gene for conferring to plants an increased tolerance to a herbicide whose target is EPSPS, comprising, in the direction of transcription, a promoter region, a transit peptide region, a sequence of a gene encoding a glyphosate tolerance enzyme and an untranslated polyadenylation signal region in 3', wherein the transit peptide region comprises, in the direction of transcription, a transit peptide of a plant gene encoding a plastid-localised enzyme, a partial sequence of the N-terminal mature pan of a plant gene encoding a plastid-localised enzyme and then a second transit peptide of a plant gene encoding a plastid-localised enzyme.

The invention also relates to any DNA sequence of the transit peptide region defined above.

The transit peptides which can be used in the transit peptide region may be known per se and may be of plant origin, for example, derived from maize, sunflower, peas, tobacco or the like. The first and the second transit peptides may be identical, analogous or different. They may in addition each comprise one or more transit peptide units. A sequence derived from the SSU of the ribulose 1,5-diphosphate carboxylase oxygenase (RuBisCO) gene is preferably used.

The partial sequence of the N-terminal mature part is derived from a plant gene encoding a plastid-localised enzyme, such as for example a maize, sunflower or pea gene or the like, it being possible for the original plant species to be identical, analogous or different from that from which the first and second transit peptides are derived respectively. Furthermore, the partial sequence of the mature part may comprise a varying number of amino acids, generally from 10 to 40, preferably from 18 to 33. A sequence derived from the SSU of the ribulose 1,5-diphosphate carboxylase oxygenase (RuBisCO) gene is preferably used.

Construction of the entire transit region may be carded out in a manner known per se, in particular by fusion or any other suitable means. The role of this characteristic region is to enable the release of a mature, native protein with a maximum efficiency.

The coding sequence for herbicide tolerance which may be used in the chimeric gene according to the invention encodes a mutant EPSPS having a degree of glyphosate tolerance. This sequence, obtained in particular by mutation of the EPSPS gene, may be of bacterial origin, for example derived from *Salmonella typhymurium* (and called in the text which follows "AroA gene"), or of plant origin, for example from petunia or from tomatoes. This sequence may comprise one or more mutations, for example the Pro 101 to Ser mutation or alternatively the Gly 96 to Ala mutations.

The promoter region of the chimeric gene according to the invention may consist advantageously of at least one promoter on a fragment thereof of a gene which is expressed naturally in plants, that is to say promoters of vital origin such as that of 35S RNA of the cauliflower mosaic virus (CaMV35S) or of plant origin such as the small subunit of the ribulose 1,5-diphosphate carboxylase (RuBisCO) gene of a crop such as maize or sunflower.

The untranslated polyadenylation signal region in 3' of the chimeric gene according to the invention may be of any origin, for example bacterial, such as the nopaline synthase gene, or of plant origin, such as the small subunit of the maize or sunflower RuBisCO.

The chimeric gene according to the invention may comprise, in addition to the above essential pans, an untranslated intermediate region (linker) between the promoter region and the coding sequence which may be of any origin, bacterial, vital or plant.

BRIEF DESCRIPTION OF THE PREFERRED EMBODIMENTS

EXAMPLE 1: CONSTRUCTION OF A CHIMERIC GENE

The construction of the chimeric gene according to the invention is carried out using the following elements:

1) "Double CaMV" promoter (that is to say pan of which has been duplicated):

The CaMV35S promoter was isolated by Odell et al. (1985). A clone, pJO 5-2, containing about 850 bp upstream of the site of initiation of transcription was cut with EcoRI-HindIII, the ends of this isolated fragment were made blunt using Klenow polymerase and the fragment inserted at the HincII site of the vector pUC19 (Yannish-Perron et al., 1985). This promoter was digested with ClaI, the ends filled using Klenow polymerase and then redigested with HindIII. A HindIII-EcoRV fragment, isolated from the same initial promoter, was introduced between these two sites. The promoter thus obtained possesses a double amplification region upstream of the regulatory elements of the CaMV35S promoter. It was introduced in the form of a HindIII-EcoRI fragment into the vector pRPA-BL 150 A alpha 2, described in French Patent Application 88/04130, cut with HindIII and EcoRI.

2) Transfer region: the two transit peptides as well as the mature protein elements used are derived from the cloned cDNA of the small subunit of the gene of maize RuBisCO whose gene has been described by Lebrun et at. (1987), and from the cloned cDNA of the small subunit of the gene of sunflower RuBisCO, isolated by Waksman et at, (1987). More specifically, the transit region, called optimised transit peptide, comprises, in the direction of translation:

- a transit peptide of the small subunit of sunflower RuBisCO,
- an N-terminal sequence of 22 amino acids of the mature part of the small subunit of maize RuBisCO,
- a transit peptide of the small subunit of maize RuBisCO.

The construct using this optimised transfer peptide is called pRPA-BL 410.

Other similar sequences may be used which contain sequences of 10 to 40 and preferably 18 and 33 amino acids respectively.

In order to provide a comparative element, another construction was carried out using a first transit peptide and the same mature sequence part but without a second transit peptide, according to the prior art (pRPA-BL 294).

3) Structural gene: it is derived from the mutant gene at the position (Pro 101 to Ser) of EPSPS of *Salmonella typhymurium* isolated by Stalker et al, (1985). The pMG34-2 clone (provided by Calgene) was linearised with XbaI and then treated with *Vigna radiata* nuclease. After recurring with SmaI, the two blunt ends were ligated. The clone obtained possesses an NcoI site in the initiator ATG as well as a 17-bp SaII site downstream of the stop codon. This clone was called pRPA-BL 104.

4) Polyadenylation signal region: the fragment is derived from the nopaline synthase gene of pTi37 (Bevan et al., 1983). This site is contained in a 260-bp MboI fragment (Fraley et at., 1983; Patent Application PCT 84/02913) which was treated with Klenow polymerase and cloned in the SmaI site of M13 mp 18 in order to introduce the BamHI and EcoRI sites at the 5' and 3' ends respectively.

After cutting with BamHI and treating with *Vigna radiata* nuclease followed by cutting with EcoRI and treating with Klenow polymerase, the resulting fragment was introduced in the vector p-BL 20 (cf. French Patent Application 88/04130), cut by XbaI and BamHI and treated with Klenow polymerase. After recutting with SaII and SstI, a fragment of about 0.4 kbp containing the 3' nos sequence on the side of the SaII site and the fight end on the T-DNA side of the SstI site is obtained.

The assembly of the various elements was carried out in the following manner:

"Transit peptide of the SSU of the maize RuBisCO/AroA gene" fusion:

The transit peptide of the SSU of the maize RuBisCO gene is derived from a 192-bp EcoRI-SphI fragment obtained from the cDNA corresponding to the SSU gene of the maize RuBisCO gene, described by Lebrun et al. (1987), possessing an NcoI site spanning the initiation codon for translation and an SphI site corresponding to the cleavage site of the transit peptide.

Translational fusion is obtained between the maize transit peptide and the bacterial EPSPS gene by treating the SphI end with bacteriophage T4 polymerase and by ligating it with the Klenow polymerase-treated NcoI end of the AroA gene from pRPA-BL 104, recur with EcoRI.

Transit peptide of the SSU of maize RuBisCO/sequence of 22 amino acids of the mature part of the SSU of maize RuBisCO/AroA gene fusion:

Similarly, a 228-bp EcoRI-HindII fragment of the cDNA of the SSU of the maize RuBisCO gene is ligated with the Klenow polymerase-treated NcoI end of the AroA gene from pRPA-BL 104 and recur with EcoRI. A translational fusion is obtained between the transit peptide of the SSU of maize RuBisCO, the 22 amino acids of the mature part of the SSU of maize RuBisCO and the bacterial EPSPS gene.

Transit peptide of the SSU of sunflower RuBisCO:

The fragment is derived from the cDNA isolated by Waksman and Freyssinct (1987). An SphI site was created at the cleavage site of the transit peptide according to the method of Zoller and Smith (1984). The transit peptide of the SSU of sunflower RuBisCO thus obtained is a 171-bp EcoRI-SphI fragment.

Transit peptide of the SSU of sunflower RuBisCO/sequence of 22 amino acids of the mature part of the SSU of maize RuBisCO/AroA gene fusion:

The construct containing the transit peptide of the SSU of maize RuBisCO/sequence of 22 amino acids of the SSU of maize RuBisCO of the mature part of the maize gene fusion was cut with 171-bp EcoRI-SphI corresponding to the transit peptide of the SSU of sunflower RuBisCO. A resulting construct exhibits a substitution of the EcoRI-SphI fragments and is a translational fusion "transit peptide of the SSU of sunflower RuBisCO/sequence of 22 amino acids of the mature part of the SSU of maize RuBisCO/AroA gene.

The EcoRI-SalI fragment was ligated with the SalI-SstI fragment containing the 3' nos sequence and the right end of the T-DNA. The resulting EcoRI-SstI fragment, comprising "transit peptide of the SSU of sunflower RuBisCO/sequence of 22 amino acids of the mature part of the SSU of maize RuBisCO/AroA gene/3' nos/T-DNA fight end", is substituted for the EcoRI-SstI fragment containing the fight end of the T-DNA of the plasmid 150 A alpha 2 containing the double CaMV promoter. The transcriptional fusion "double CaMV/transit peptide of the SSU of sunflower RuBisCO/sequence of 22 amino acids of the mature pan of the SSU of maize RuBisCO/AroA gene/3' nos" in the vector 150 A alpha 2 was called pRPA-BL 294.

"Transit peptide of the SSU of sunflower RuBisCO/sequence of 22 amino acids of the SSU of maize RuBisCO/transit peptide of the SSU of maize RuBisCO/AroA gene" fusion:

The above construct is cut with NcoI-HindIII, releasing the Area gene. Next it is ligated with a 1.5 kbp NcoI-HindIII fragment containing the "transit peptide of the SSU of maize RuBisCO/AroA gene" fusion. A resulting construct exhibits a substitution of the NcoI-HindIII fragments and is a translational fusion "transit peptide of the SSU of sunflower RuBisCO/sequence of 22 amino acids of the SSU of the RuBisCO of the mature part of the maize gene/transit peptide of the SSU of maize RuBisCO/AroA gene".

The EcoRI-SalI fragment was ligated with the SalI-SstI fragment containing the 3' nos sequence and the right end of the T-DNA. The resulting EcoRI-SstI fragment comprising "transit peptide of the SSU of sunflower RuBisCO/sequence of 22 amino acids of the SSU of the RuBisCO of the mature part of the maize gene/transit peptide of the SSU of maize RuBisCO/AroA gene/3' nos/T-DNA fight end" is substituted for the EcoRI-SstI fragment containing the right end of the T-DNA of the plasmid 150 A alpha 2 containing the double CaMV promoter. The transcriptional fusion "double CaMV/transit peptide of the SSU of sunflower RuBisCO/sequence of 22 amino acids of the SSU of the RuBisCO of the mature part of the maize gene/transit peptide of the SSU of maize RuBisCO/AroA gene/3' nos" in the vector 150 A alpha 2 was called pRPA-BL 410.

EXAMPLE 2: RESISTANCE OF THE TRANSFORMED PLANTS

1. Transformation:

The vector is introduced into the nononcogenic agrobacterium strain EHA 101 (Hood et al., 1987) carrying the cosmid pTVK 291 (Komari et al., 1986). The transformation method is based on the procedure of Horsh et al. (1985).

2. Regeneration:

The regeneration of the tobacco PBD6 (source SEITA France) using foliar explants is carried out on a Murashige and Skoog (MS) basic medium containing 30 g/l of sucrose and 200 g/ml of kanamycin. The foliar explants are removed from greenhouse- or in vitro-grown plants and transformed according to the foliar disc method (Science 1985, Vol. 227, p. 1229–1231) in three successive stages: the first comprises the induction of shoots on an MS medium supplemented with 30 g/l of sucrose containing 0.05 mg/l of naphthylacetic acid (ANA) and 2 mg/l of benzylaminopurine (BAP), for 15 days. The shoots formed during this stage are then developed by culturing on an MS medium supplemented with 30 g/l of sucrose, but not containing hormone, for 10 days. The developed shoots are then removed and they are cultured on an MS planting medium containing half the content of salts, vitamins and sugars and not containing hormone. After about 15 days, the deeply-rooted shoots are placed in soil.

3. Measurement of the glyphosate tolerance:

a) In vitro: the tolerance is measured by weighing the mass of calluses extrapolated to 100 foliar discs of 0.5 cm in diameter, after 30 days of growth on an MS medium supplemented with 30 g/l of sucrose, 0.05 mg/l of naphthaleneacetic acid and 2 mg/l of BAP containing 35 ppm of glyphosate and 200 micrograms/ml of kanamycin. Under these conditions, it is observed that for the tobacco plants modified by the chimeric gene of pRPA BL 410 according to the invention, the mass of calluses is 34 g whereas for the plants modified by the chimeric gene without a second transit peptide, the mass is only 12 g.

b) In vivo: 30 plants derived from the regeneration of the tobaccos transformed using pRPA-BL 294 and pRPA-BL 410 respectively are transferred to a greenhouse and treated at the 5-leaf stage by spraying with an aqueous suspension at a dose corresponding to 0.6 kg/ha of glyphosate (Round up). After 21 days, a phenotypic examination is carded out of the plants relative to untransformed control plants. Under these conditions, it is observed that the plants transformed using pRPA-BL 410 possess a negligible phytotoxicity whereas the control plants are completely destroyed; moreover, the plants transformed using a chimeric gene, which differs from the preceding one by the absence of a second transit peptide, possess a phytotoxicity of not less than 30% destruction.

These results clearly show the improvement brought by the use of a chimeric gene according to the invention for the same gene encoding the glyphosate tolerance.

The transformed plants according to the invention may be used as parents for producing lines and hybrids having an increased tolerance to glyphosate.

EXAMPLE 3

Spring colzas, Westar cultivar, resistant to glyphosate, were obtained using the method of BOULTER et al., 1990 (Plant Science, 70:91–99), with pRPA-BL410. These plants were resistant to a greenhouse treatment with glyphosate at 400 g a.s/ha, a treatment which destroys nontransgenic plants.

We claim:

1. A chimeric gene for conferring to plants an increased tolerance to glyphosate comprising, in the direction of transcription, a promoter region, a DNA sequence encoding a first transit peptide from a ribulose-1,5,-bisphosphate carboxylase small subunit, a DNA sequence encoding an N-terminal domain of a mature ribulose-1,5-bisphosphate carboxylase small subunit, a DNA sequence encoding a second transit peptide from a ribulose-1,5,-bisphosphate carboxylase small subunit, coding sequence for 5-(enolpyruvyl)shikimate-3-phosphate synthase and an untranslated polyadenylation signal.

2. The chimeric gene according to claim 1 wherein the coding sequence for 5-(enolpyruvyl)shikimate-3-phosphate synthase is of bacterial origin.

3. The chimeric gene according to claim 1 wherein the coding sequence for 5-(enolpyruvyl)shikimate-3-phosphate synthase is of plant origin.

4. A vector for transforming plants, which comprises a chimeric gene according to claim 1.

5. A vector for transforming plants, which comprises a chimeric gene according to claim 2.

6. A vector for transforming plants, which comprises a chimeric gene according to claim 3.

7. An Agrobacterium, which contains a vector according to claim 4.

8. An Agrobacterium, which contains a vector according to claim 5.

9. An agrobacterium, which contains a vector according to claim 6.

10. A transformed plant cell, which contains a chimeric gene according to claim 1.

11. A transformed plant cell, which contains a chimeric gene according to claim 2.

12. A transformed plant cell, which contains a chimeric gene according to claim 3.

13. A transformed plant with improved glyphosate tolerance, which was obtained by regeneration of the cell according to claim 10.

14. A transformed plant with improved glyphosate tolerance, which was obtained by regeneration of the cell according to claim 11.

15. A transformed plant with improved glyphosate tolerance, which was obtained by regeneration of the cell according to claim 12.

16. A plant according to claim 13, which is a dicotyledon.

17. A plant according to claim 13, which is a monocotyledon.

18. A process for constructing a chimeric gene according to claim 1, wherein sequences for at least two transit peptide regions, at least one sequence of the N-terminal domain of a mature ribulose-1,5-bisphosphate carboxylase small subunit, at least one sequence encoding 5-(enolpyruvyl) shikimate-3phosphate synthase and a polyadenylation signal region are each isolated, and wherein said sequences are then assembled in the direction of transcription of the 5-(enolpyruvyl) shikimate-3phosphate synthase gene.

19. A process for constructing a chimeric gene according to claim 2, wherein sequences for at least two transit peptide regions, at least one sequence of the N-terminal domain of a mature ribulose-1,5-bisphosphate carboxylase small subunit, at least one sequence encoding 5-(enolpyruvyl) shikimate-3-phosphate synthase and a polyadenylation signal region are each isolated, and wherein said sequences are then assembled in the direction of transcription of the 5-(enolpyruvyl) shikimate-3-phosphate synthase gene.

20. A process for constructing a chimeric gene according to claim 3, wherein sequences for at least two transit peptide regions, at least one sequence of the N-terminal domain of a mature ribulose-1,5-bisphosphate carboxylase small subunit, at least one sequence encoding 5-(enolpyruvyl) shikimate-3-phosphate synthase and a polyadenylation signal region are each isolated, and wherein said sequences are then assembled in the direction of transcription of the 5-(enolpyruvyl) shikimate-3-phosphate synthase gene.

*21. An agronomic method comprising:*

*A) growing a plant which contains in its genome a nucleic acid sequence encoding a polypeptide sufficient for localization of a gene product in a chloroplast of a plant cell, which polypeptide comprises in the direction of translation:*

*(i) a first chloroplast transit peptide of a ribulose-1,5-bisphosphate carboxylase oxygenase small subunit;*

*(ii) an N-terminal domain from a mature ribulose-1,5-bisphosphate carboxylase oxygenase small subunit; and*

*(iii) a second chloroplast transit peptide of a ribulose-1,5-bisphosphate carboxylase oxygenase small subunit;*

*and further encoding a 5-(enolpyruvyl)shikimate-3-phosphate synthase which renders said plant tolerant to a phosphonomethyl glycine herbicide; and*

*B) applying said herbicide to the plant.*

*22. The method of claim 21, wherein the plant is maize.*

*23. The method of claim 21, wherein the 5-(enolpyruvyl) shikimate-3-phosphate synthase is mutated, the mutation being selected from the group consisting of Pro 101 to Ser and Gly 96 to Ala.*

*24. The method of claim 23, wherein the plant is maize.*

* * * * *